US008919347B2

(12) United States Patent
Carlson et al.

(10) Patent No.: US 8,919,347 B2
(45) Date of Patent: Dec. 30, 2014

(54) SUPPORT SURFACE COVER HAVING DIFFERENT FRICTIONAL ZONES

(75) Inventors: J. Martin Carlson, Mora, MN (US); Mark J. Payette, Lino Lakes, MN (US); Mark N. Manzella, Maplewood, MN (US)

(73) Assignee: Tamarack Habilitation Technologies, Inc., Blaine, MN (US)

( * ) Notice: Subject to any disclaimer, the term of this patent is extended or adjusted under 35 U.S.C. 154(b) by 286 days.

(21) Appl. No.: 13/262,081

(22) PCT Filed: Apr. 20, 2010

(86) PCT No.: PCT/US2010/031695
§ 371 (c)(1), (2), (4) Date: Sep. 29, 2011

(87) PCT Pub. No.: WO2010/123857
PCT Pub. Date: Oct. 28, 2010

(65) Prior Publication Data
US 2012/0037169 A1 Feb. 16, 2012

Related U.S. Application Data

(60) Provisional application No. 61/171,863, filed on Apr. 23, 2009.

(51) Int. Cl.
*A61F 13/00* (2006.01)
*D04B 7/04* (2006.01)
*A61G 5/10* (2006.01)
*A61G 7/057* (2006.01)

(52) U.S. Cl.
CPC .............. *A61G 5/1043* (2013.01); *A61G 7/057* (2013.01)
USPC ............................................ 128/889; 66/196

(58) Field of Classification Search
USPC ......... 128/889, 846; 66/196; 139/420 R, 421, 139/410, 407; 5/420, 630, 636, 490, 495, 5/499, 500, 502; 602/41–42, 52, 54, 57
See application file for complete search history.

(56) References Cited

U.S. PATENT DOCUMENTS 4,571,960 A 2/1986 Hursh et al.
4,572,174 A * 2/1986 Eilender et al. ............... 128/889

(Continued)

FOREIGN PATENT DOCUMENTS

JP 2003024201 A 1/2003
WO 0025642 A1 5/2000

(Continued)

OTHER PUBLICATIONS

PCT International Search Report, Dec. 30, 2010.

(Continued)

*Primary Examiner* — Patricia Bianco
*Assistant Examiner* — Ophelia A Hawthorne
(74) *Attorney, Agent, or Firm* — Westman, Champlin & Koehler, P.A.; Z. Peter Sawicki; Amanda Prose

(57) ABSTRACT

An apparatus is disclosed for placement on a support surface between the support surface and a living being, wherein the living being has a bony prominence. The apparatus includes a first zone having a first coefficient of friction, the first zone being configured for positioning proximate the bony prominence. A second zone is adjacent the first zone, the second zone having a second coefficient of friction higher than the first coefficient of friction. The second zone is configured for positioning remote from the bony prominence. A method of preventing or healing decubitus ulcers includes positioning the bony prominence over the first zone and positioning an area remote from the bony prominence over the second zone.

18 Claims, 12 Drawing Sheets

(56) References Cited

U.S. PATENT DOCUMENTS

| | | | |
|---|---|---|---|
| 4,615,188 A | | 10/1986 | Hursh et al. |
| 4,843,844 A | | 7/1989 | Hursh et al. |
| 4,873,982 A | | 10/1989 | Morrison |
| 5,111,544 A | * | 5/1992 | Graebe ............................ 5/654 |
| 5,127,119 A | | 7/1992 | Rogers |
| 5,638,558 A | | 6/1997 | Moore |
| 5,787,523 A | * | 8/1998 | Lindberg .................. 5/81.1 HS |
| 6,108,820 A | | 8/2000 | Bernhardt |
| 6,145,132 A | | 11/2000 | Towner |
| 6,633,830 B2 | * | 10/2003 | Chen et al. .................... 702/155 |
| 6,918,140 B1 | | 7/2005 | Cooper |
| 7,281,549 B2 | | 10/2007 | Metzger |
| 2004/0123391 A1 | | 7/2004 | Call |
| 2005/0125901 A1 | | 6/2005 | Nichols |
| 2007/0220673 A1 | | 9/2007 | Nichols |
| 2007/0277282 A1 | | 12/2007 | Sheppell |
| 2008/0121305 A1 | | 5/2008 | Metzger |
| 2008/0264512 A1 | | 10/2008 | Metzger |

FOREIGN PATENT DOCUMENTS

| | | |
|---|---|---|
| WO | 2004050002 A1 | 6/2004 |
| WO | 2010039524 A2 | 4/2010 |

OTHER PUBLICATIONS

UK Examination Report; GB1117730.0; Dec. 19, 2012.

Baby Gadget retail listing, undated, see the A-Z duvet cover, accessed Jan. 14, 2014. available from http://www.babygadget.net/2006/11/b__is__for__bedtime__with__the__az__d.php.

All Things Infant retail listing, undated, see the JOIe Alphabet Cot Duvet Set, accessed Jan. 14, 2014. available from http://www.allthingsinfant.co.nz/webapps/p/93835/266071/954903.

Heirloom Linens retail listing, undated, see the E-Z Peasy Kids Bedding, accessed Jan. 14, 2014, available from http:// www.heirloomlinens.com/productaspx?ProductID=960&deptid=64&ProceCat=1&Lang=EN-US&SID=6c4acaa9-dfc2-495c-b140-479fd3c41255.

Etsy retail listing, undated, see the Classic Alphabet Pillow Cover, accessed Jan. 14, 2014, available from http://www.etsy.com/listing/73817948/classic-alphabet-pillow-cover-blue-and.

Art Fire retail listing, undated, see the Monogram Letter Pillow Cover, accessed Jan. 14, 2014, available from http://www.artfire.com/ext/shop/product__view/comfyheaven/7745040/monogram__letter__pillow__cover__black__and__white__18__inch__-ns01.

Running With Scisors craft instruction, undated, see the Ampersand Decor Pillow tutorial, accessed Jan. 14, 2014, available from http://www.running-w-scissors.com/2011/03/ampersand-decor-pillow.html.

Examination Report for GB1117730.0, Jan. 17, 2014.

* cited by examiner

SUPPORT SURFACE COVER HAVING DIFFERENT FRICTIONAL ZONES

CROSS-REFERENCE TO RELATED APPLICATION

This Application is a Section 371 National Stage Application of International Application No. PCT/US2009/057991 filed Sep. 23, 2009 and published as WO 2010/039524 A2 on Apr. 8, 2010, the content of which is hereby incorporated by reference in its entirety.

BACKGROUND

Decubitus ulcers (also known as pressure ulcers) afflict many people. Those who spend long periods of time on support surfaces such as wheelchairs and beds are particularly vulnerable.

The sitting position of a wheelchair user focuses significant loads on a small area; namely, the buttocks and surrounding areas. Carlson J M, Payette M J, Vervena L P, "Seating orthosis design for prevention of decubitus ulcers," J Prosth & Orth, Spring 1995; 7(2): 51-60. Wheelchair users often sit for prolonged periods; moreover, the physiology of many wheelchair users (e.g., geriatric or paraplegic) makes them more prone to ulcer formation. Bennett L, Kavner D, Lee B Y, Trainor F S, Lewis J M, "Skin stress and blood flow in sitting paraplegic patients," Arch Phys Med Rehabil., April 1984; 65(4):186-90. With regard to people with spinal cord injury (SCI)—most of whom use wheelchairs—between a third and a half develop ulcers within five years after the injury. Five to seven percent of people with SCI eventually require hospitalization due to decubitus ulcers and seven to eight percent eventually die of complications from ulcers. Agram L, Gefen A, "Pressure ulcers and deep tissue injury: a bioengineering perspective," Journal of Wound Care, Vol. 16, Iss. 8, 1 Sep. 2007, pp 336-342.

Overall, the incidence rates for all kinds of decubitus ulcers range from 0.4% to 38% in acute care, 2.2% to 23.9% in long-term care, to 0% to 17% in home care. More than 2.5 million pressure ulcers are treated each year in the United States. Estimates put United States expenditures on the treatment of decubitus ulcers as high as $11 billion. Reddy M, Gill S S, Rochon P A, "Preventing pressure ulcers: a systematic review," JAMA, 23 Aug. 2006; 296(8): 974-84.

Most decubitus ulcers form over weightbearing bony prominences. In seating, the most frequently involved areas are over the sacrum, coccyx, ischial tuberosities and greater trochanters. Carlson et al., Spring 1995. For people in beds, other involved areas can include those over the back of the heels, the back of the head, the elbows, and the shoulder blades, for example.

Two forms of external loading play a role in the formation of decubitus ulcers: pressure and shear. Friction forces act parallel (or tangential) to the skin surface and produce shear strains within the skin and underlying tissue. Both pressure and shear harm skin. Carlson et al., Spring 1995.

For many years, care providers focused predominantly on alleviating pressure when evaluating support surfaces and wheelchair cushions. Reducing pressure is accomplished by redistributing the overall contact pressure. Carlson et al., Spring 1995. This commonly involves off-loading pressure from a vulnerable area to a less vulnerable area.

Like pressure, shear is also reduced by lowering peak pressure because shear is caused by two phenomena: pressure and friction. In the context of seat cushions and other support surfaces, there are several reasons to focus on shear reduction.

First, in relative terms, shear is more destructive of tissue integrity than pressure. Bennett et al., April 1984. Second, in some instances, it may be easier to manage friction and shear than it is to manage pressure. Third, most efforts to control peak pressure involve foam materials that can accelerate ulcer formation by impeding heat dissipation and evaporation.

SUMMARY

An apparatus is disclosed for placement on a support surface between the support surface and a living being, wherein the living being has a bony prominence. The apparatus comprises a first zone having a first coefficient of friction, the first zone being configured for positioning proximate the bony prominence. A second zone is adjacent the first zone, the second zone having a second coefficient of friction higher than the first coefficient of friction. The second zone is configured for positioning remote from the bony prominence.

A method of preventing or healing decubitus ulcers comprises positioning the bony prominence over the first zone and positioning an area remote from the bony prominence over the second zone.

BRIEF DESCRIPTION OF THE DRAWINGS

The disclosed subject matter will be further explained with reference to the attached figures, wherein like structure or system elements are referred to by like reference numerals throughout the several views.

DETAILED DESCRIPTION

The present disclosure presents an apparatus and method for preventing the formation of decubitus ulcers by managing shear forces. The present disclosure relates to a cover for a support surface such as a seat cushion or a bed mattress, said cover having zones of low friction and higher friction. The cover is constructed such that zones of low friction are positioned proximate tissue that is vulnerable to the formation of decubitus ulcers. Zones of higher friction are positioned proximate less vulnerable tissue; these higher friction zones help to provide support for a living being such as a person.

Shear can be mitigated by increasing the "slipperiness" (i.e., reducing the coefficient of friction (COF)) in an interface between the skin and the support surface.

If we define:

Lf as the friction load,

Lp as the load perpendicular to the skin surface (pressure type load), and

COF as the coefficient of friction of the interface,

It is desirable that Lf≤Lp×COF.

Managing friction and shear does not simply mean attempting to eliminate all friction. Friction may be essential for proper positioning of a person or retention of a person on a support surface. For example, there is often a tendency for a seated person to slide forward in a chair. Without friction, the person could even slide out of the chair or wheelchair. Similarly, for a bed, it may not be desirable that the entire bearing surface be low friction. This may be especially true of areas near the lateral sides of the bed, where too little friction could cause a person to slide out of the bed. Therefore, having a higher friction zone in particular locations on a support surface may be beneficial.

The present disclosure presents a way to manage friction and shear by controlling the COF of an interface between the skin and a surface supporting a human body (or other living being). This allows for the management of friction and shear without changing the structure of the underlying support device. In an exemplary embodiment, an apparatus such as a cover for a support surface is secured to the support surface rather than to a part of the body. The apparatus can cover all or a portion of a support surface. The apparatus has one or more zones of low friction on a support surface so that vulnerable parts of the body can be subjected to lower friction and shear loads. The apparatus also has one or more zones of higher friction on a support surface so that less vulnerable parts of the body can be subjected to higher friction and shear loads; additionally or alternatively, the zones of higher friction on a support surface can be used for beneficial purposes such as the positioning of a person on the support surface or the retention of the person in a desired position.

Figure 1:
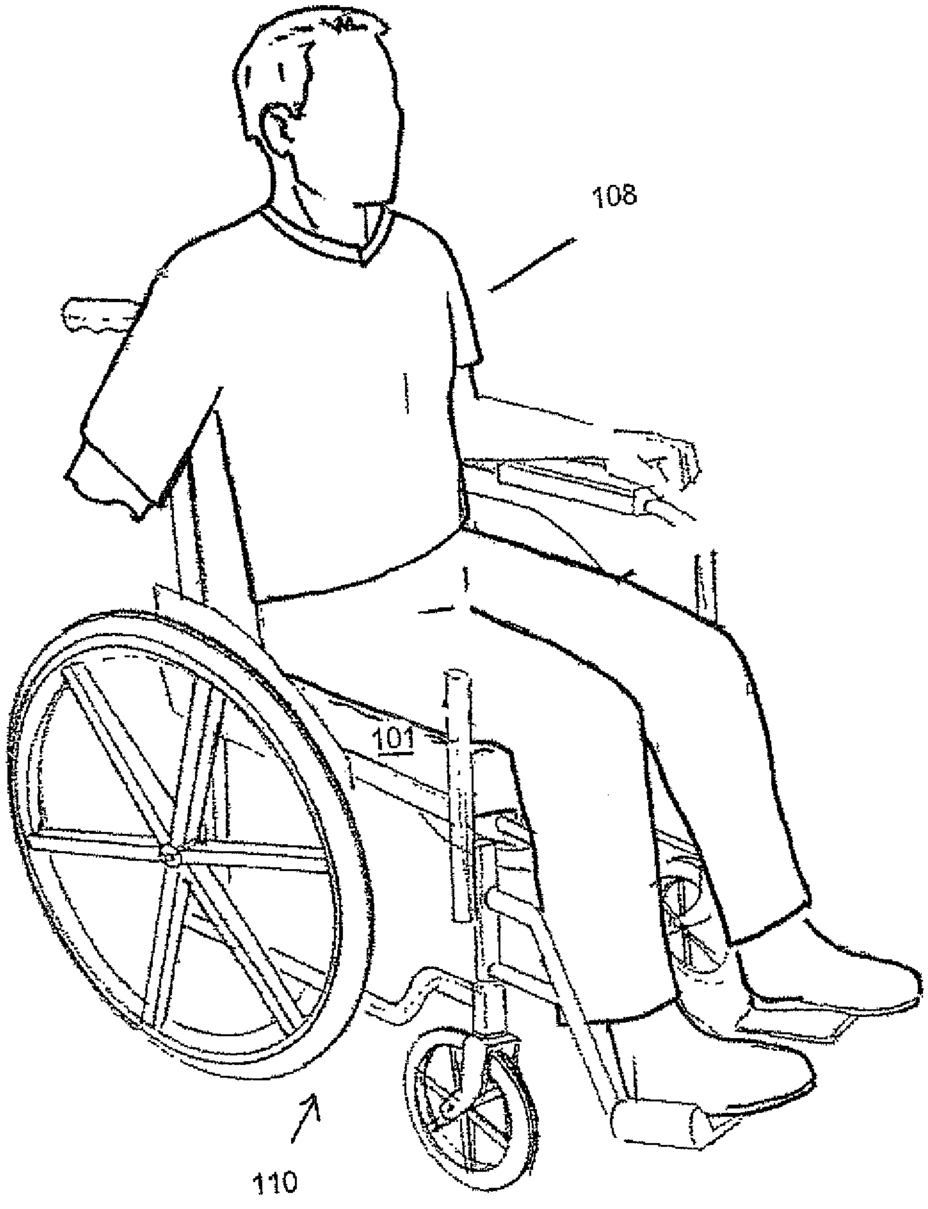
FIG. 1 is a perspective view of a person sitting in a wheelchair on a cushion with a cover according to a first embodiment of the disclosure.
Figure 2:
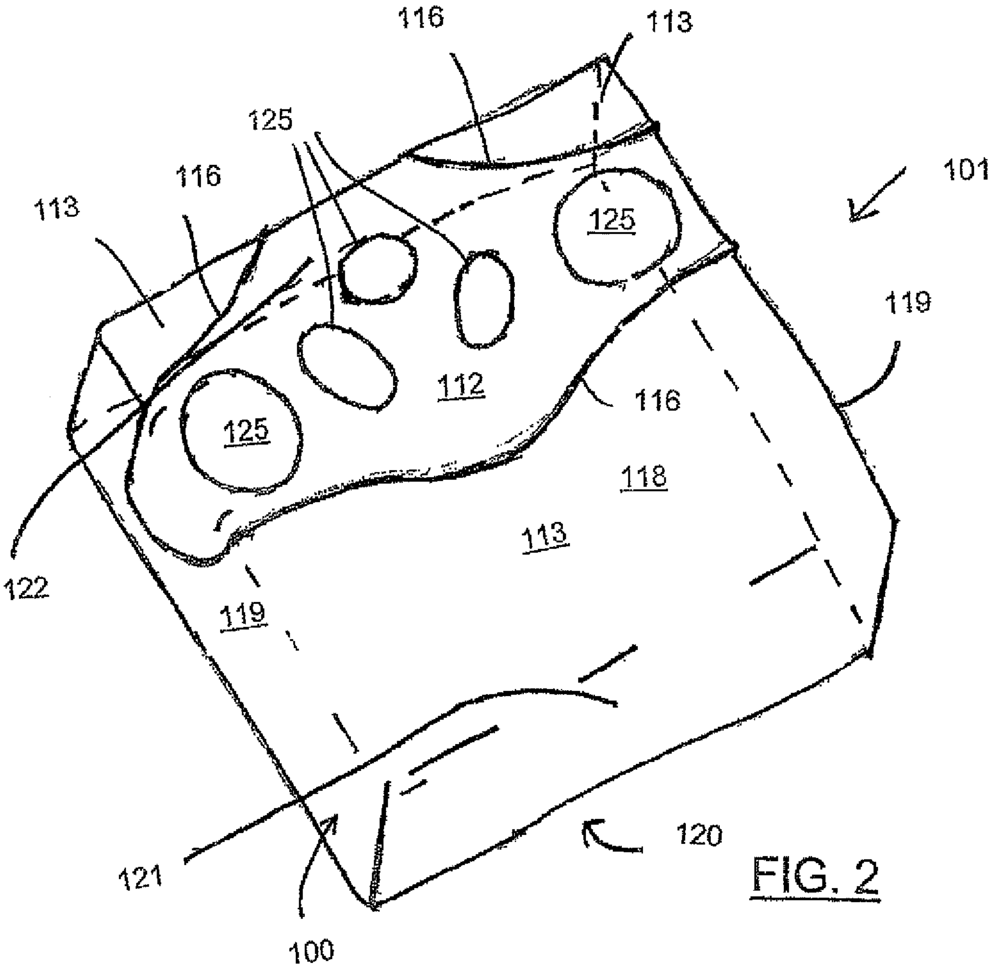
FIG. 2 is a perspective view of a wheelchair cushion with a cover according to a first embodiment of the disclosure.

An exemplary embodiment of a cover 100 for a seat cushion 101, the cover 100 incorporating first zones of low friction 112 and second zones of higher friction 113, is shown in FIGS. 1-2. In an exemplary application, cushion 101 is used on the seat of a wheelchair 110.

As mentioned above, most decubitus ulcers form over weight-bearing bony prominences of people who spend long periods of time sitting or lying down. In seating, the most frequently involved areas are tissue over the coccyx 103, ischial tuberosities 104*a*, 104*b* and greater trochanters 105*a*, 105*b*, as illustrated in lower body 111 of FIG. 3. Carlson et al. 1995. Thus, the areas of a person's skin near bony prominences 103, 104*a*, 104*b*, 105*a*, 105*b* need the most protection from shear stresses caused by friction.

Some areas of the body in contact with the seat cushion 101 can better withstand the effects friction and shear. Generally, these are areas more remote from bony prominences 103, 104*a*, 104*b*, 105*a*, 105*b* such as parts of the gluteal regions 106*a*, 106*b* and the undersides of the thighs 107*a*, 107*b*.

Figure 3:
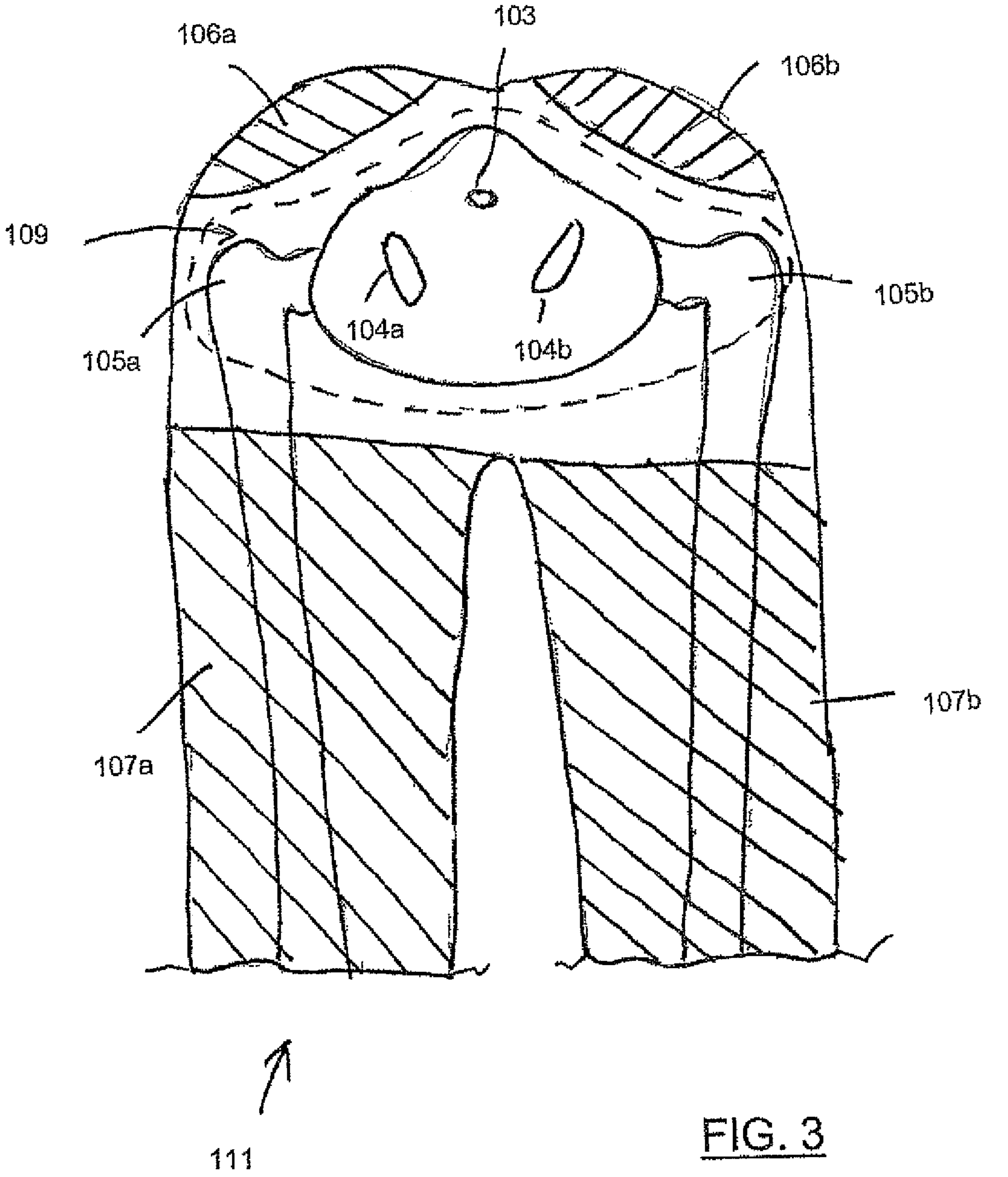
FIG. 3 is a rear, anatomical schematic of the buttocks area of a person, including the skeleton.

For purposes of support surface design for seated persons 108, therefore, the area of greatest concern for decubitus ulcer formation can be identified. If one were to draw a dotted line around these bony prominences 103, 104*a*, 104*b*, 105*a*, 105*b*, as shown in FIG. 3, the area within the dotted line can be considered the primary area of tissue vulnerability 109. For many seated persons 108, managing friction and shear in this area of tissue vulnerability 109 can be critical.

The design of the seat cushion cover 100 can take into account the susceptibility of various regions of the body to skin trauma. The seat cushion cover 100 can have zones of low friction 112 and zones of higher friction 113. The low friction zones 112 of the seat cushion cover 100 can be positioned proximate the primary area of tissue vulnerability 109. Thus, when the person 108 is sitting on the seat cushion 101, the low friction zone 112 can be positioned proximate the bony prominences such as the ischial tuberosities 104*a*, 104*b*, the coccyx 103, and the greater trochanters 105*a*, 105*b*. FIG. 2 shows possible contact areas 125 on the cover 100 corresponding to the bony prominences 103, 104*a*, 104*b*, 105*a*, 105*b*. All of these contact areas 125 are within the zone of low friction 112 in an exemplary embodiment. If the seated person 108 is positioned in this way, the low friction zone 112 forms a low friction interface between the skin proximate these bony prominences 103, 104*a*, 104*b*, 105*a*, 105*b* and the seat cushion 101. This can reduce the shear loads transferred to tissues near these bony prominences 103, 104*a*, 104*b*, 105*a*, 105*b*.

On the other hand, the higher friction zones 113 can be positioned proximate parts of the body more distant from bony prominences 103, 104*a*, 104*b*, 105*a*, 105*b* and therefore less vulnerable to skin trauma—such as parts of the gluteal regions 106*a*, 106*b* and the undersides of the thighs 107*a*, 107*b*. Areas more remote from bony prominences 103, 104*a*, 104*b*, 105*a*, 105*b* are less susceptible to the formation of decubitus ulcers because more tissue can dissipate shear forces. Areas remote from bony prominences 103, 104*a*, 104*b*, 105*a*, 105*b* can serve to support the seated person 108 and to keep the seated person 108 well-positioned in the wheelchair 110 and on the cushion 101. For example, friction against the undersides of the thighs 107*a*, 107*b* can prevent the seated person 108 from sliding forward on the cushion 101. With regard to the higher friction zone 113 in the front part 121 of the cushion 101, this can serve as a less slippery location on which to place a hand (or place a transfer board) when the seated person 108 re-positions herself or himself or transfers into or out of the wheelchair 110.

The low friction zone 112 can be created in a variety of ways. One way is to create the zone 112 from a material having a slippery surface. One such material is a film made of polytetrafluoroethylene (PTFE) or other similar material. Films such as those made of PTFE can form interfaces with other materials (such as clothing, skin, etc.) with extremely low COF's. In an exemplary embodiment, the film is cut into the shape of the low friction zone 112 and attached to the top 118 of the cover 100. In this way the slippery surface of the low friction zone 112 is exposed and can therefore form an interface with the clothing or skin of the seated person 108.

However, polymer films such as those made from PTFE can have potential disadvantages. Films made from materials such as PTFE generally lack elasticity and breathability. The lack of elasticity can be particularly problematic in a cover 100 for a seat cushion 101 because tension loads in a cover material can transfer to a bony prominence. Fabrics can also be utilized for the low friction zone 112. However, many fabrics with low COFs do not exhibit much elasticity.

Figure 4:
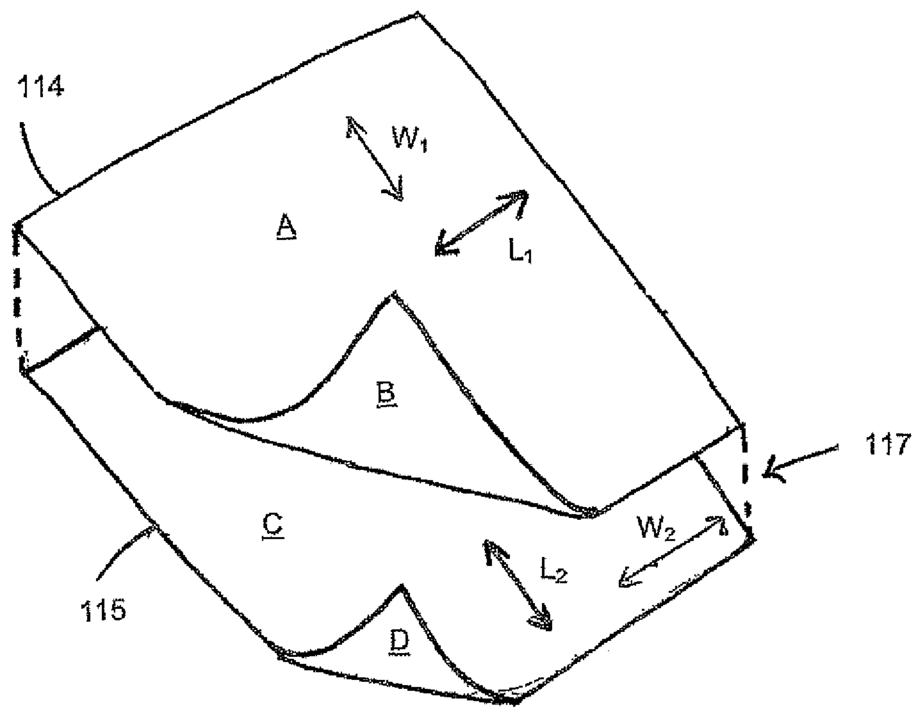
FIG. 4 is a perspective view of two pieces of fabric forming an interface according to an exemplary embodiment of the disclosure.

Another way to create the low friction zone 112 can be to employ a layered fabric construction. FIG. 4 shows a portion of two-ply, stretchable fabric construction 117. When the faces of certain fabric sheets are oriented in a particular way with respect to each other and allowed to slide freely against each other, a low friction interface can be created.

In the illustrated example, a first ply 114 having a top major surface A and a bottom major surface B forms the top layer of construction 117. The second ply 115 has a top major surface C and bottom major surface D. Each of the first ply 114 and second ply 115 exhibits anisotropy, wherein there is a different physical property of the material when measured along different axes in a plane of the material corresponding to the orientation of a major surface. Each of the first ply 114 and the second ply 115 has a relatively shiny major surface. In the illustrated embodiment, the bottom major surface B of the first ply 114 and the top major surface C of the second ply 115 are the relatively shiny major surfaces of each layer. The first and second plies 114, 115 are arranged as shown: the bottom major surface B of the first ply 114 and the top major surface C of the second ply 115 contact each other to form an interface in construction 117. At this interface, the first and second plies 114, 115 move relatively freely in relation to each other, with low friction therebetween. Thus, the interface has a low COF.

Many different fabrics can be used to form the two-ply construction 117. One suitable fabric for both plies 114, 115 is Style 480 Spandex distributed by Cooper Fabrics of Norwood, Mass. This is a three-bar tricot fabric consisting of 85% 40-denier semi-dull nylon and 15% 140-denier spandex. To form the interface 117, the plies 114, 115 are oriented with each other in the following way: sides B and C face each other as mentioned above. When using this particular kind of fabric, sides B and C are shinier than sides A or D. In other words, the shiny sides of the two plies 114, 115 face each other.

Second, the length $L_1$ of the first ply 114 and the length $L_2$ of the second ply 115 are arranged so they are not parallel and are preferably substantially perpendicular, as shown in FIG. 4. The lengths $L_1$ and $L_2$ of the first ply 114 and the second ply 115 can be considered the machine direction. The machine direction is the direction parallel to the forward movement of material through the knitting or weaving machine during the fabric's manufacture. In the case of the Style 480 Spandex from Cooper Fabrics, the machine direction is the same as the direction of greatest stretch. When arranged in the fashion described above, the interface in construction 117 demonstrates a very low coefficient of friction (COF).

The length directions $L_1$ and $L_2$ of the plies 114, 115 do not have to be arranged precisely perpendicular. In addition, when in use, the plies 114, 115 will slide out of a perpendicular relationship. However, the closer the lengths $L_1$ and $L_2$ of the plies 114, 115 remain perpendicular to one another, the lower the COF of the interface 117 will be.

Figure 5:
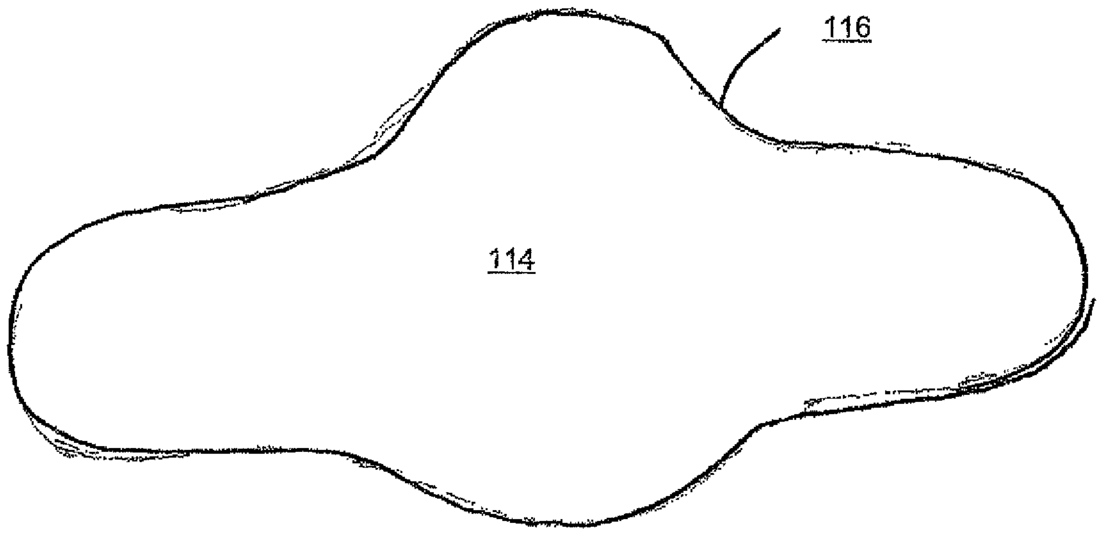
FIG. 5 is a plan view of the first ply of the cover according to an exemplary embodiment of the disclosure.

The first ply 114 can be a layer cut or fabricated generally in the shape of the low friction zone 112 shown in FIGS. 2 and 5. The perimeter 116 of the first ply 114 can be attached to the top side C of the second ply 115. Attachment can be in a variety of ways, including by sewn seams, adhesives, ultrasonic welding, or other methods. The second ply 115 with side C facing up can cover the entire cushion 101 and wrap around the sides 119, bottom 120, front 121, and back 122 of the cushion 101. The fabric of the second ply 115 can be elastic and can be stretched somewhat taut on the cushion 101. In this way, the second ply 115 can help keep the cover 100 on the cushion 101. Retention of the cover 100 could be accomplished in a variety of other ways, such as with the use of elastic bands or drawstrings, for example (not shown).

A cover 100 using the Style 480 fabric demonstrates excellent elastic deformation characteristics. A single ply of the fabric that can be used in the higher friction zones 113 can stretch 270% in the $L_1$ direction and 90% in the $W_1$ direction. The two-ply combination construction 117 that can be used in the low friction zone 112 would demonstrate lower stretch capabilities. For example, stretch in the $L_1$ direction of the first ply 114 would be limited by the stretch of second ply 115 in the $W_2$ direction, i.e., limited to a stretch of 90%.

The elasticity of the cover 100 can be enhanced in a variety of ways. First, an elastic seam can join the first ply 114 and second ply 115 at the perimeter 116 of the first ply 114. Examples of stitches for an elastic seam include a three-step zig-zag also known as a multi-step zig-zag (such as that made on a Singer Tradition sewing machine with a stitch length setting of two and one half); single-step zig-zag; overlock (serger); and cover stitch. Using an elastic stitch can help prevent the seam from restricting the stretch of the cover 100. Moreover, use of a three-step zig-zag or multi-step zig-zag stitch can also prevent a sewn seam from bunching. Preventing bunching can be desirable both aesthetically and for the comfort of the seated person 108.

Second, the $L_2$ direction of the second ply 115 of the cover 100 can be oriented from side-to-side of the seat cushion 101 rather than front-to-back. This can maximize the elasticity of the cover 100 in the side-to-side direction of the seat cushion 101. Since the greater trochanters 105*a*, 105*b* will likely be positioned near the sides 119 of the of the seat cushion 101, it is the side-to-side direction that may be in most need of additional elasticity to avoid "tenting" of the cover 100 over the greater trochanters 105*a*, 105*b*.

Figure 6:
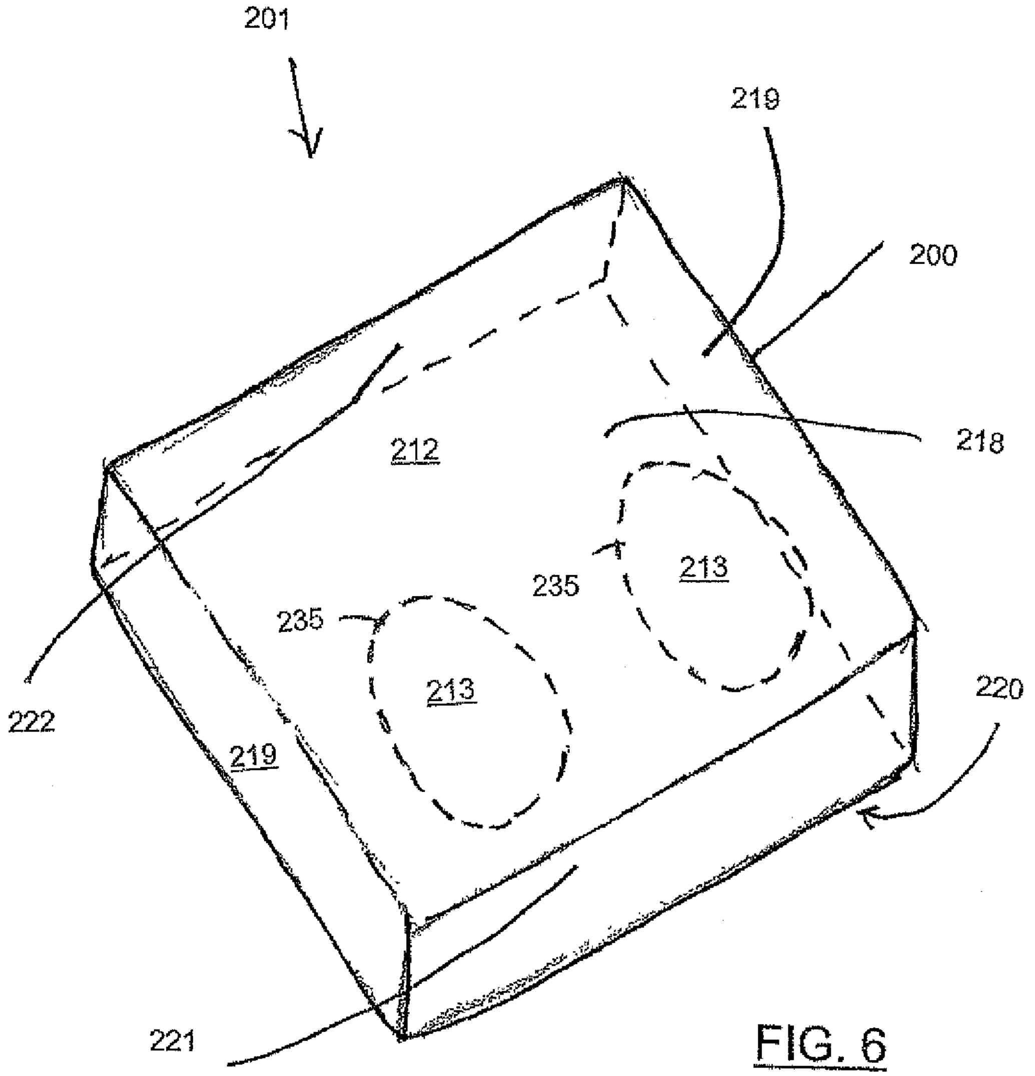
FIG. 6 is a perspective view of a wheelchair cushion with a cover according to yet another exemplary embodiment of the disclosure.

Another exemplary embodiment of a cover 200 for a seat cushion 201 is illustrated in FIG. 6. In the illustrated embodiment, two higher friction zones 213 in the cover 200 are positioned so that when a person 108 sits on the seat cushion 201 having the cover 200, the higher friction zones 213 are located underneath the thighs 107*a*, 107*b*. The rest of the cover 200 can be a low friction zone 212. In an exemplary embodiment, cover 200 encloses the entire cushion 201 and wraps around the sides 219, bottom 220, front 221, and back 222 of the cushion 201.

One way to construct the cover 200 is to first make the entire cover 200 out of the two-ply fabric construction 117 described above. Then, holes are cut in the first ply 114 in the oval shapes 235 at the locations shown in FIG. 6. By cutting the oval shapes 235, the two-ply fabric interface is eliminated in these areas, resulting in higher friction zones 213. Thus, the undersides of the thighs 107*a*, 107*b* can rest on the higher friction zones 213.

Figure 7:
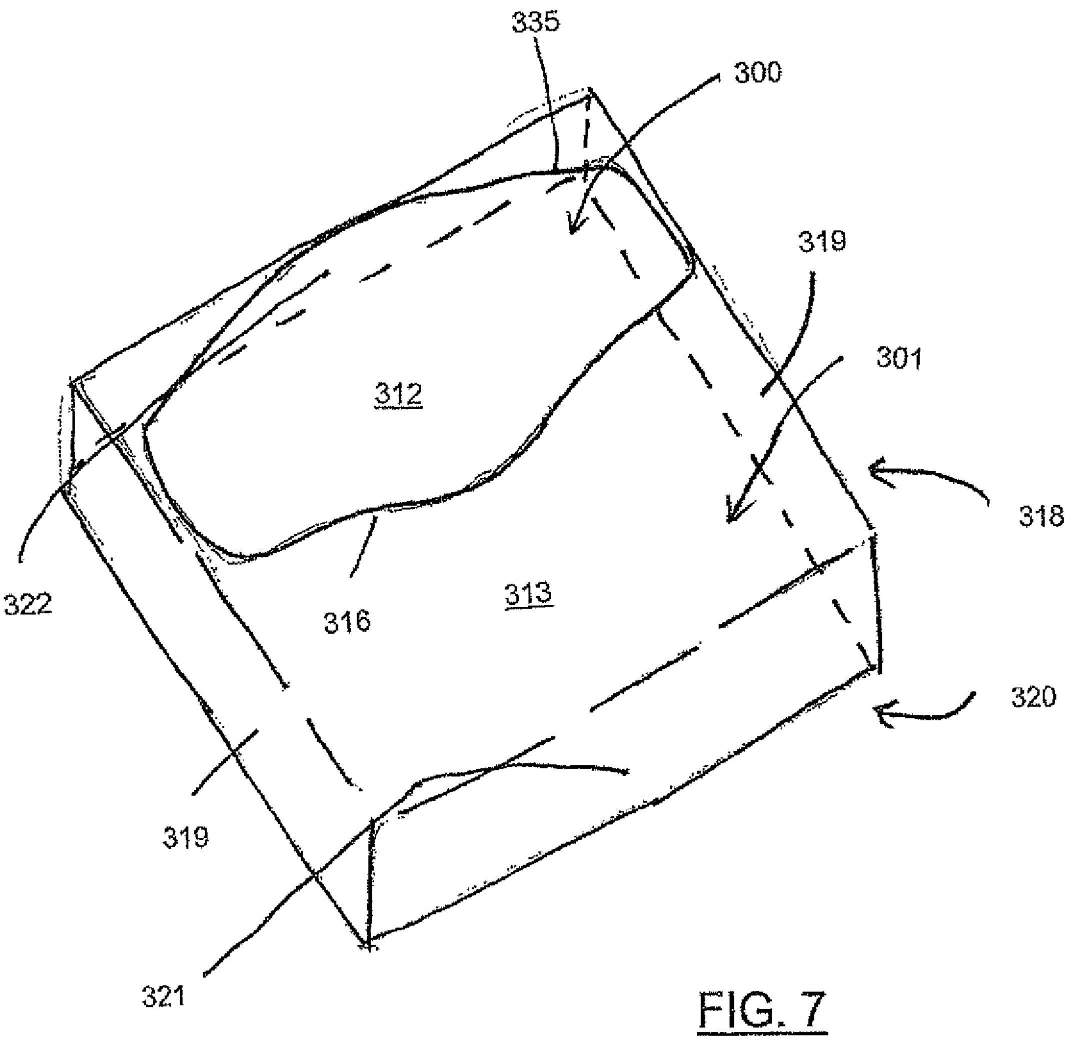
FIG. 7 is a perspective view of a wheelchair cushion with a cover according to still another exemplary embodiment of the disclosure.

Another exemplary embodiment of a cover 300 for a seat cushion 301 is shown in FIG. 7. As illustrated, cover 300, whose shape 335 is defined by perimeter 316, covers only a portion of the seat cushion 301. Therefore the cover 300 is only a partial cover. The entire cover 300 can comprise a low friction zone 312. The exposed portion of the top 318 of the seat cushion 301 (or another cover) can comprise the higher friction zone 313 in a case where the cushion 301 has a non-slippery surface. In one embodiment, the cover 300 is in the form of a patch that can be attached to the seat cushion 301 or other support surface in various ways, including, for example, the use of pressure sensitive adhesive. The cover 300 can form a low friction zone 312 by having a slippery surface or by incorporating a low COF interface such as with the two-ply construction 117 described above. In an exemplary embodiment, cover 300 does not wrap around the sides 319, bottom 320, front 321, or back 322 of the cushion 301.

Figure 8:
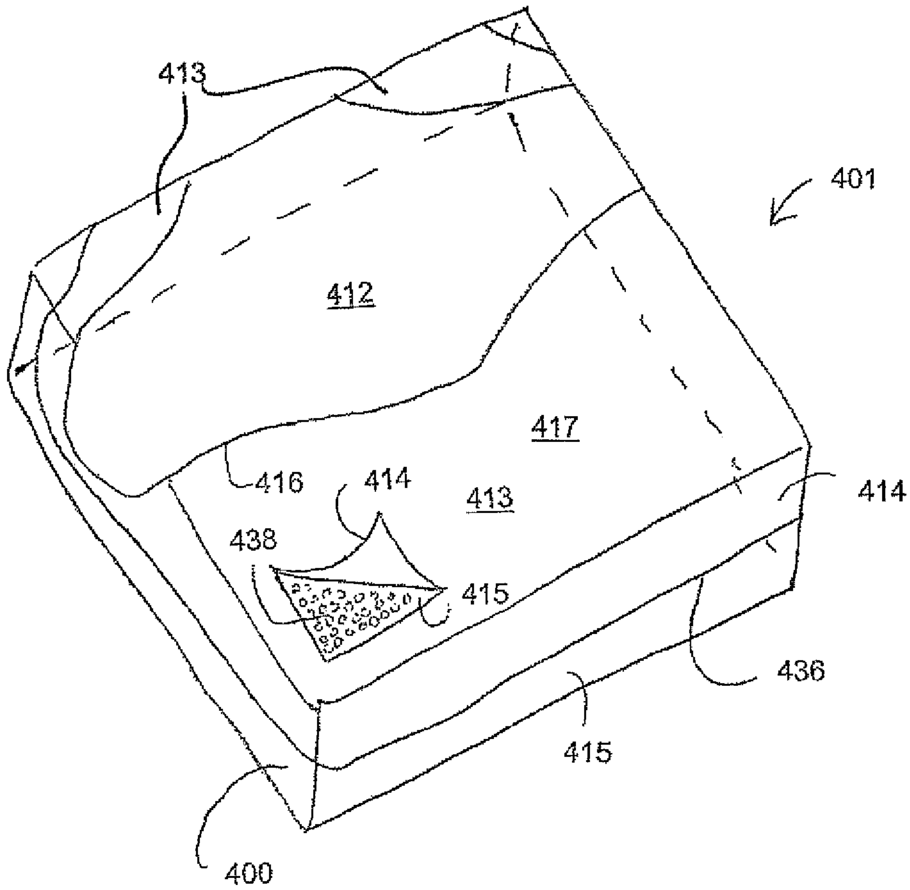
FIG. 8 is a perspective view of a wheelchair cushion with a cover according to another exemplary embodiment of the disclosure.

Yet another exemplary cover 400 for a seat cushion 401 is shown in FIG. 8. In the illustrated example, a two-ply, stretchable fabric construction 417 has a perimeter 436 and encompasses a low friction zone 412 and a higher friction zone 413. The higher friction zone 413 is formed by applying a friction appliment 438 between the two plies of fabric 414, 415. In FIG. 8, a portion of first ply 414 is cut and lifted so that the friction appliment 438 on second ply 415 can be seen. In normal use, friction appliment 438 is not visible because it is positioned between first ply 414 and second ply 415. In an exemplary embodiment, friction appliment 438 is applied by screen printing Plastisol Ink onto side C, the shiny side, of the second ply 415. Friction appliment 438 can also or alternatively be applied onto side B, the shiny side, of the first ply 414. Other methods of applying a friction appliment 438, such as spraying, brushing, or dripping can also be used. Low friction zone 412 is formed by omitting the application of friction appliment 438 between the first ply 414 and the second ply 415 in areas where low friction is desired.

Friction appliment 438 can be used to create zones with differing COF. In the higher friction zone 413, a friction appliment 438 can be a series of round dots, approximately 1/16" in diameter, evenly spaced in a rectangular pattern at approximately 8 dots per linear inch, approximately 64 dots per square inch and lightly screen printed to create an opaque deposit of ink approximately 0.004 inches thick on Style 480 Spandex from Cooper Fabric. Changing the friction appliment 438 diameter, spacing, application thickness or material properties can alter a zone's COF. For example, a zone of intermediate friction could be created by altering the application of the friction appliment 438. A friction appliment 438 can also be used on a cover for another type of support surface, such as a bed mattress.

A sewn seam can be used to attach the first ply 414 to the second ply 415 at a perimeter 436. Some types of sewn seams can reduce elasticity in a cover 400. For this reason many wheelchair users 108 prefer a cover 400 without sewn seams in areas needing the greatest elasticity. By using a friction appliment 438 to create higher friction zone 413 and omitting the use of friction appliment 438 to create lower friction zone 412, no seams are required at the perimeter 416 between the higher friction zone 413 and the lower friction zone 412. Thus, other seams may be easily positioned away from areas of the cover 400 that may come in contact with vulnerable tissue.

Figure 9:
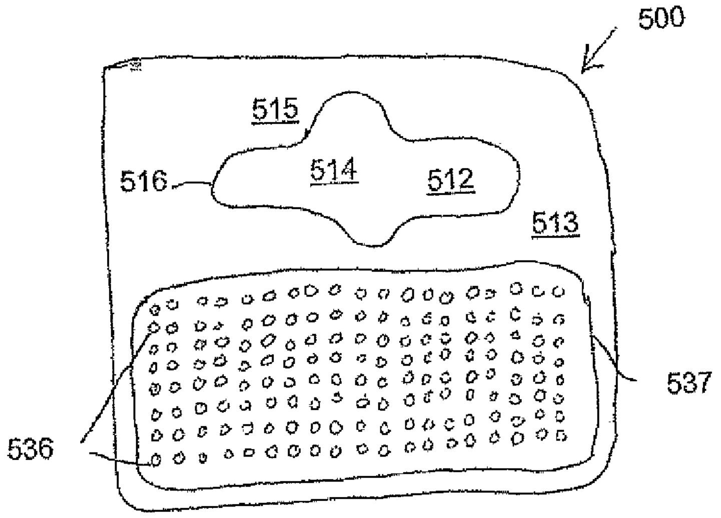
FIG. 9 is a plan view of a cover for wheelchair cushion according to another exemplary embodiment of the disclosure.

Another cover 500 for a seat cushion 101 is shown in FIG. 9. In the illustrated embodiment, a two-ply, stretchable fabric construction comprising first ply 514 and second ply 515 is used for a low friction zone 512, which has perimeter 516, surrounded by higher friction zone 513. A friction appliment 536 reduces sliding of cover 500 with respect to a cushion 101. Other methods of helping to retain the cover 500 on a cushion 101 may be used separately or in combination with friction appliment 536. Friction appliment 536 is applied within a friction appliment zone 537 to cover 500 on a side of cover 500 that will be in contact with cushion 101. In an exemplary embodiment, fiction appliment zone 537 is positioned under the thighs of a seated person 108. Friction appliment 536 can be a series of round dots, approximately 1/16" in diameter, evenly spaced in a rectangular pattern with approximately 8 dots per linear inch, approximately 64 dots per square inch and lightly screen printed to create an opaque deposit of ink approximately 0.004 inches thick on Style 480 Spandex from Cooper Fabric. A friction appliment can also be used to keep and/or retain a cover on other types of support surfaces such as a bed mattress.

In yet another exemplary embodiment, friction appliment 536 is applied within friction appliment zone 537 to cover 500 on a side of cover 500 that will be in contact with the seated person 108. Accordingly, the friction appliment 536 can help prevent the seated person 108 from sliding with respect to cover 500. In an exemplary embodiment, friction appliment zone 537 is remote from vulnerable tissue. A friction appliment could also be used on a cover for other types of support surfaces such as a bed mattress.

Figure 10:
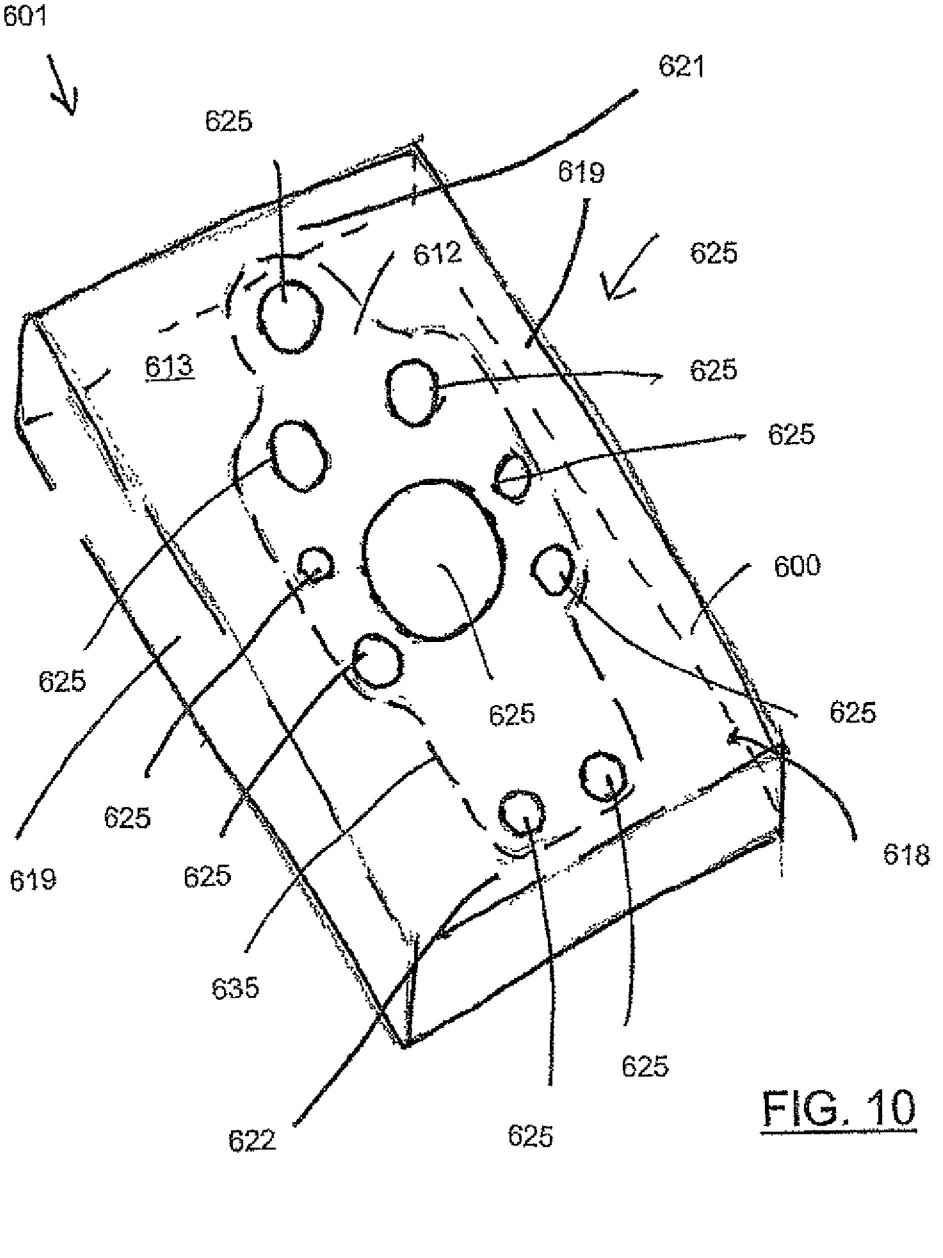
FIG. 10 is a perspective view of a cover for a mattress according to an exemplary embodiment of the disclosure.

An exemplary embodiment of a bed cover 600 is shown in FIG. 10. Cover 600 is used on a bed mattress 601 and incorporates a zone of low friction 612 and a zone of higher friction 613. In one exemplary embodiment, cover 600 replaces the bottom, fitted sheet for a mattress 601 and covers at least the top 618 of the mattress 601. Cover 600 can help prevent and heal decubitus ulcers of people lying for prolonged periods in beds.

Figure 11:
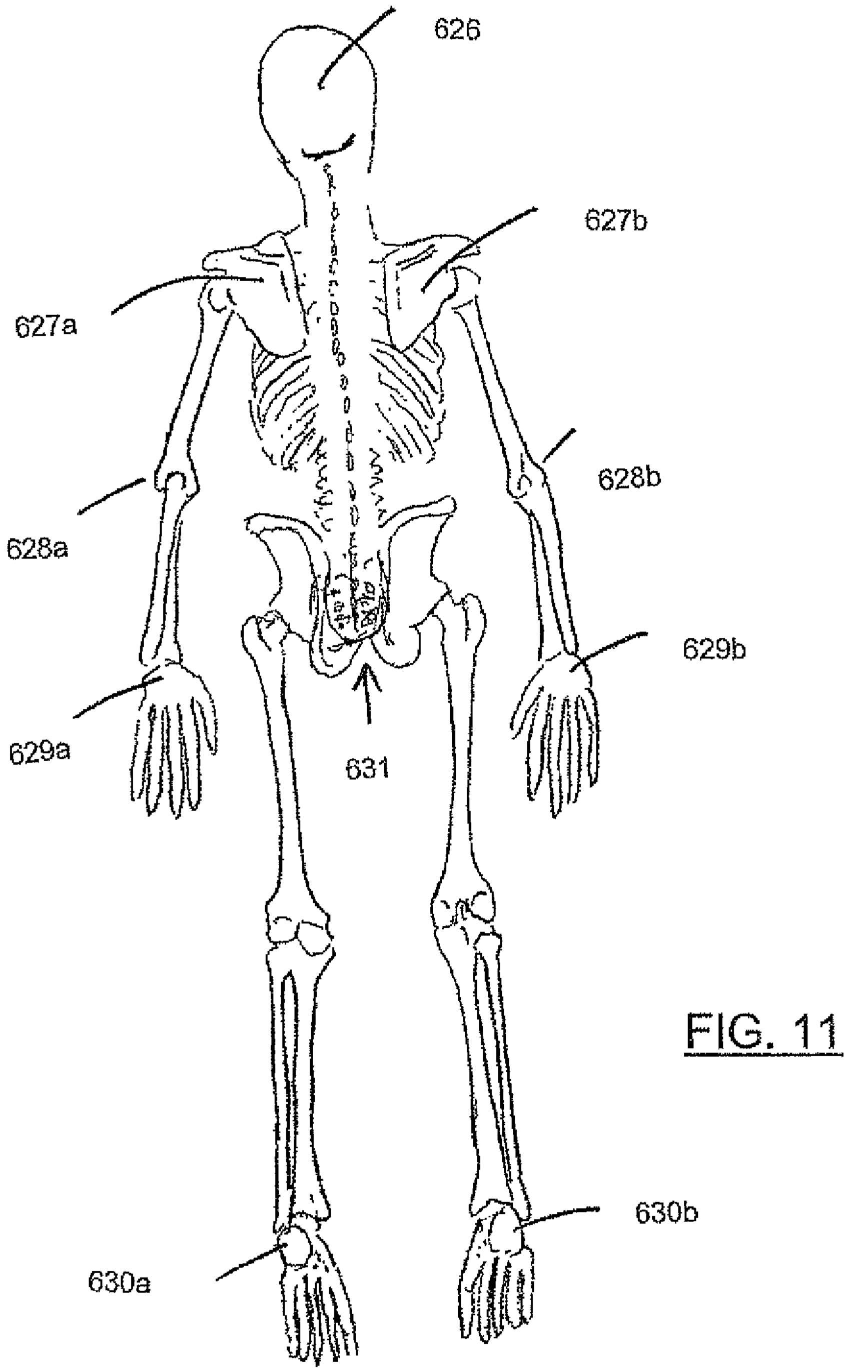
FIG. 11 is a rear anatomical view of a human skeleton.

The cover 600 can generally be constructed in the same way as the seat cushion covers 100, 200, 300, 400, 500 described above, though there may be some differences. The cover 600 is sized and constructed to fit onto a standard mattress 601 used in a hospital, long-term care facility, or a home. A portion of the cover 600 can be a low friction zone 612, which can have the shape 635. This shape 635 circumscribes contact areas 625 for bony prominences such as the occipital bone 626; the shoulder blades 627*a*, 627*b*; the elbows 628*a*, 628*b*; the hands 629*a*, 629*b*; the lower part of the spinous process 631; and the heels of the feet 630*a*, 630*b*, as shown in FIG. 11. These are areas that can be especially susceptible to the formation of decubitus ulcers for persons lying in bed.

The higher friction zone 613 along the lateral sides of the bed can prevent a person from sliding out of the bed. It can also allow a visitor or a caregiver, for example, to sit on the side of the bed without sliding off. The higher friction zone 613 along the lateral sides also allows for the secure positioning of transfer boards on the side of the bed. Finally, the higher friction zone 613 on the sides 619, head 621, and foot 622 of the mattress 601 can help secure top sheets or blankets tucked underneath the mattress 601.

Figure 12:
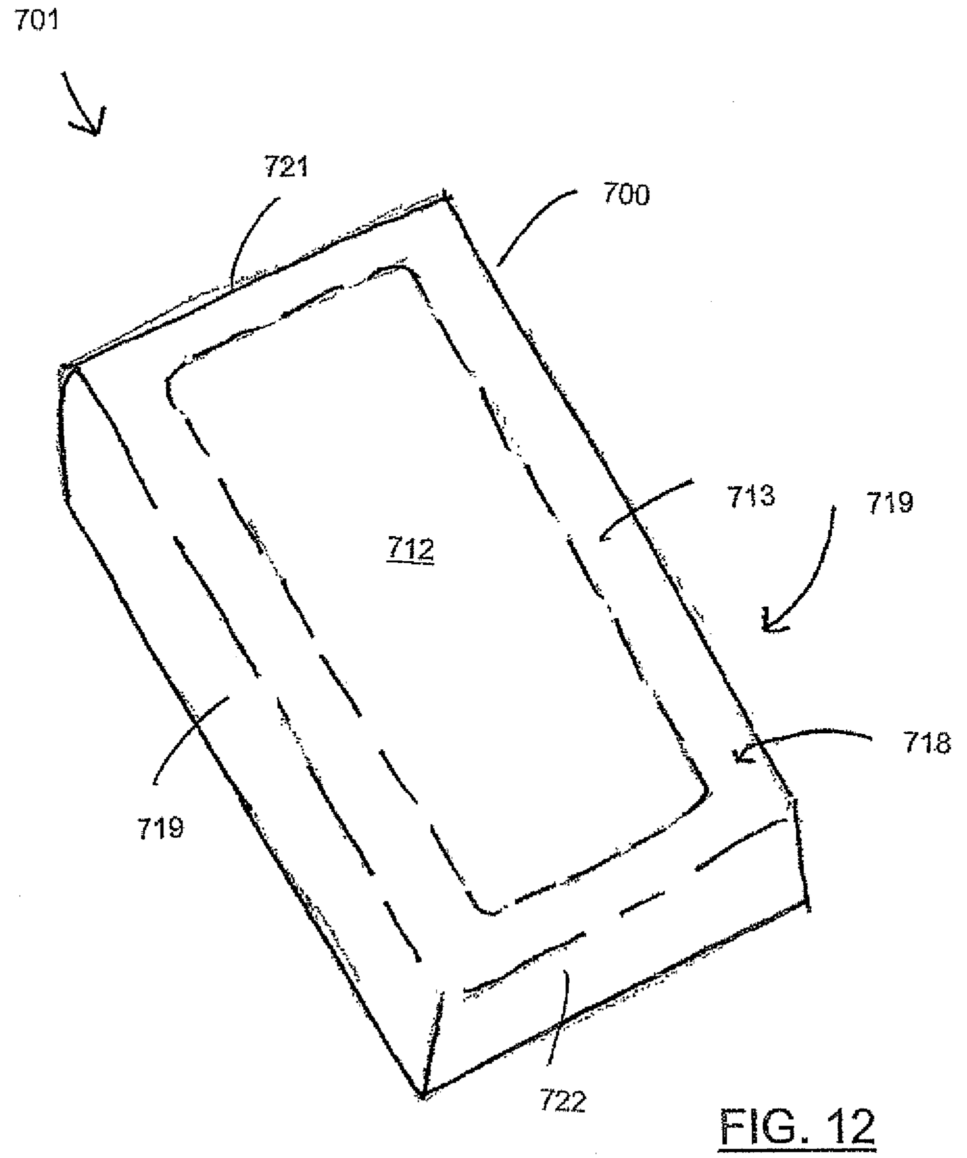
FIG. 12 is a perspective view of a cover for a mattress according to another exemplary embodiment of the disclosure.

Another exemplary embodiment of a cover 700 is shown in FIG. 12. In the illustrated embodiment, the low friction zone 712 has a substantially rectangular shape, promoting ease of manufacture. In one exemplary embodiment, cover 700 replaces the bottom, fitted sheet for a mattress 701 and covers at least the top 718 of the mattress 701. The higher friction zone 713 along the lateral sides also allows for the secure positioning of transfer boards on the side of the bed. Moreover, the higher friction zone 713 on the sides 719, head 721, and foot 722 of the mattress 701 can help secure top sheets or blankets tucked underneath the mattress 701.

The disclosed support surface cover is used on a wheelchair or chair cushion or a bed mattress in exemplary embodiments. The cover need not extend completely over or conceal a support surface. The support surface cover could, for example, be merely placed upon a support surface without a means of fixable attachment. On the other hand, a support surface cover could also be fixably attached to a support surface.

Many other configurations for seat cushion covers and support surface covers with low friction and higher friction zones are conceivable. Zones of various dimensions, shapes, and locations can be employed. For example, the low friction zone of a seat cover could make up the back two-thirds, the back half, or the back one-third of the seat cushion (not shown). For other people or for animals other than humans, different areas of vulnerability than those depicted above may exist. In such instances, zones of low friction and higher friction can be formed to meet the needs of the person or animal being supported. These variations and many others are within the scope of this disclosure.

The present disclosure should not be considered limited to the particular examples described above. For example, while suitable sizes, materials, fasteners, and the like have been disclosed in the above discussion, it should be appreciated that these are provided by way of example and not of limitation, as a number of other sizes, materials, fasteners, and so forth may be used without departing from the invention. Various modifications as well as numerous structures to which the present disclosure may be applicable will be readily apparent to those of skill in the art to which the present disclosure is directed upon review of the present specification. The claims, which arise from this application, are intended to cover such modifications and structures. In addition, any feature disclosed with respect to one embodiment may be incorporated in another embodiment, and vice-versa.

Although the present invention has been described with reference to preferred embodiments, workers skilled in the art will recognize that changes may be made in form and detail without departing from the spirit and scope of the invention.

What is claimed is:

1. An apparatus for placement on a support surface between the support surface and a living being, the living being having a bony prominence, the apparatus comprising: an interface having a first zone, the first zone having a first coefficient of friction, the first zone configured for positioning proximate the bony prominence; and a second zone adjacent the first zone, the second zone having a second coefficient of friction higher than the first coefficient of friction, the second zone configured for positioning remote from the bony prominence, wherein the first zone comprises a two-ply fabric construction, each ply having a machine direction, wherein the machine direction of the first ply is oriented substantially perpendicular to the machine direction of the second ply and wherein the first zone and the second zone occupy different areas on the same side of the interface.

2. The apparatus of claim 1 constructed as a seat cushion cover.

3. The apparatus of claim 2 wherein the second zone is configured for positioning proximate a thigh of the living being.

4. The apparatus of claim 2 comprising a fabric oriented to maximize elasticity in a side-to-side direction.

5. The apparatus of claim 1 constructed as a bed mattress cover.

6. The apparatus of claim 5 wherein the first zone is positioned on a central portion of a top of a mattress.

7. The apparatus of claim 5 wherein the second zone is positioned along a side of a top of a mattress.

8. The apparatus of claim 1 wherein the two-ply fabric construction comprises: a first ply having a machine direction, a first major surface and a second major surface, wherein the second major surface is shinier than the first major surface; and a second ply having a machine direction, a first major surface and a second major surface, wherein the second major surface is shinier than the first major surface; wherein the second major surface of the first ply contacts the second major surface of the second ply, and wherein the machine direction of the first ply is not parallel to the machine direction of the second ply.

9. The apparatus of claim 8 wherein the first ply has a perimeter, and wherein the first ply is joined to the second ply at the perimeter of the first ply.

10. The apparatus of claim 8 wherein the first ply and second ply are joined by an elastic seam.

11. The apparatus of claim 1 wherein the second zone comprises a two-ply fabric construction.

12. The apparatus of claim 11 wherein the second zone further comprises a friction appliment disposed between the two plies.

13. The apparatus of claim 11 wherein the friction appliment is disposed adjacent the support surface.

14. The apparatus of claim 1 wherein the second zone comprises a friction appliment.

15. The apparatus of claim 1 wherein the first zone comprises a coated fabric.

16. The apparatus of claim 1 wherein the first zone comprises polytetrafluoroethylene.

17. The apparatus of claim 1 constructed as a partial cover for a support surface.

18. A method for preventing or healing decubitus ulcers comprising positioning a living being having a bony prominence on a support surface apparatus comprising an interface having a first zone comprising two-plies, each ply having a machine direction and the first ply oriented substantially perpendicular to the second ply with respect to the machine direction of each ply and having a first coefficient of friction and a second zone adjacent the first zone, the second zone having a second coefficient of friction higher than the first coefficient of friction, wherein the first zone and the second zone occupy different areas on the same side of the interface, the method comprising: positioning the bony prominence over the first zone; and positioning an area remote from the bony prominence over the second zone.

* * * * *